(12) United States Patent
Schertiger et al.

(10) Patent No.: US 9,023,013 B2
(45) Date of Patent: May 5, 2015

(54) CATHETER KIT FOR A URINARY CATHETER

(75) Inventors: Lars Olav Schertiger, Fredensborg (DK); Kim Becker, Hilleroed (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/517,263

(22) PCT Filed: Dec. 17, 2010

(86) PCT No.: PCT/DK2010/050346
§ 371 (c)(1),
(2), (4) Date: Jun. 20, 2012

(87) PCT Pub. No.: WO2011/076211
PCT Pub. Date: Jun. 30, 2011

(65) Prior Publication Data
US 2012/0271282 A1    Oct. 25, 2012

(30) Foreign Application Priority Data
Dec. 21, 2009 (DK) .................... 2009 70285

(51) Int. Cl.
| | | |
|---|---|---|
| B65D 83/10 | (2006.01) |
| A61M 25/00 | (2006.01) |
| A61B 5/00 | (2006.01) |
| A61M 27/00 | (2006.01) |
| A61B 19/02 | (2006.01) |
| A61M 25/01 | (2006.01) |

(52) U.S. Cl.
CPC ....... A61M 25/0111 (2013.01); A61M 25/0017 (2013.01); A61M 25/002 (2013.01)

(58) Field of Classification Search
CPC ...... B65D 83/10; A61M 25/00; A61M 27/00; A61B 5/00; A61B 19/02
See application file for complete search history.

(56) References Cited

U.S. PATENT DOCUMENTS

| | | | |
|---|---|---|---|
| 4,051,849 A | | 10/1977 | Poncy |
| 4,204,527 A | * | 5/1980 | Wu et al. ............... 600/575 |
| 6,086,008 A | * | 7/2000 | Gray et al. ............. 242/388.6 |
| 2001/0000263 A1 | * | 4/2001 | Baumgartner ........... 606/146 |
| 2004/0163980 A1 | * | 8/2004 | Tanghoj et al. ......... 206/363 |
| 2005/0251108 A1 | * | 11/2005 | Frassica ................. 604/540 |
| 2009/0071851 A1 | * | 3/2009 | Maki et al. ............. 206/210 |
| 2009/0277988 A1 | * | 11/2009 | Hernik ................. 242/478.2 |

FOREIGN PATENT DOCUMENTS

| | | |
|---|---|---|
| GB | 2033231 | 6/1983 |
| GB | 2284764 | 8/1998 |
| WO | 03002179 | 1/2003 |
| WO | 2008138351 | 12/2003 |

* cited by examiner

*Primary Examiner* — Tatyana Zalukaeva
*Assistant Examiner* — Sara Sass
(74) *Attorney, Agent, or Firm* — Coloplast Corp., Coloplast A/S; Nick Baumann

(57) ABSTRACT

A urinary catheter kit is provided. The catheter kit includes a catheter with a flared end and a package provided with interior protrusions for cooperating with the flared end of the catheter. The largest outer diameter of the flared end of the catheter is slightly larger than the smallest diameter of the package at the protrusions. Thereby, the protrusions will function as a backstop for the catheter. The rigidity of the catheter at the flared end is selected so that—depending on the angle of the flared end—the flared end will be able to flip over if it is subjected to a force over a predetermined level. Thereby the catheter will be able to be entered back into the package.

11 Claims, 2 Drawing Sheets

CATHETER KIT FOR A URINARY CATHETER

The invention relates to a catheter kit for a urinary catheter comprising a package and a urinary catheter. The urinary catheter is provided with a flared end and the package is provided with interior protrusions adapted for cooperating with the flared end.

BACKGROUND

Urinary catheters are used as a tool assisting in the draining of the urinary bladder of persons that have reduced or non-existing bladder control. The reduced or non-existing bladder control may either be temporary or permanent, where a temporary loss of bladder control may be caused by for example trauma, loss of consciousness or illness. An example of a permanent loss of bladder control may be where a loss of a neural connection between the brain or spinal cord and the urinary bladder occurs due to a trauma to the spinal cord, as is often the case with para- and tetraplegics.

One example of a urinary catheter which is widely used for draining urine from the urinary bladder, is where a catheter tube is inserted into the urethra of a user and where the tip of the catheter tube is maneuvered into the urinary bladder, forcing the urethral sphincter open and thus providing a drainage channel from the urinary bladder and out of the body, via the catheter tube. There are two types of catheters which are commonly used, the permanent catheter and the intermittent catheter. The permanent catheter is a highly flexible catheter which is inserted by medical professionals into the body for a long period of time, up to 12 weeks, and where the catheter is anchored inside the bladder. The intermittent catheter is usually a single use catheter or a multiple use catheter, which is inserted by the user into the urethra/bladder for the immediate drainage of their urinary bladder and is removed from the urethra/bladder following the drainage. The following disclosure will primarily be concentrated on the intermittent urinary catheter.

DESCRIPTION OF RELATED ART

There are a number of different types of intermittent catheters which are currently available for the user, such as SpeediCath™ and EasiCath™ marketed by Coloplast A/S. These are conventional one-piece catheter tubes which have an outlet at their distal end that may be used to connect the catheter to a urinary bag for collecting the urine drained from the urine bladder.

Another type of a catheter is disclosed in WO 03/002179 which is a telescopic catheter, where one of the telescopic elements is the catheter package and another telescopic element is the catheter member that telescopes from the catheter package. The telescopic catheter is collapsed during storage and transport and extended for insertion into the urethra, providing female users with a compact and discrete catheter which may be used anywhere and without any significant preparation time.

Another type of catheter is disclosed in WO 2008/138351 which discloses a telescopic device having a first tubular member and an extension member having a coupling member that limits the displacement of the extension member within the first tubular member, where the coupling member engages the interior of the first tubular member. This device is a telescopic intermittent catheter, which is also adapted for the use by a male user, where the first tubular member is adapted in such a way that both telescopic members are adapted to be inserted into the urethra of the user.

The telescopic catheters known in the art, as discussed above, are locked in their extended state, such that the extension member or the telescopic element is prevented from collapsing into their compacted state. This means that upon disposal of the catheter, possibly after use, either into a trash bin or back into a storage area, such as a handbag or a pocket, it is difficult to dispose of the catheter discretely.

Thus, there is a need for a telescopic device that, during extension, can be prevented from collapsing. Furthermore, the device may be collapsed into a collapsed state.

SUMMARY OF THE INVENTION

The invention concerns a urinary catheter kit including a package and a catheter. The catheter has a flared end and the package has ribs or other protrusions extending inwards in the package. The flared end is adapted in its outermost diameter to cooperate with the smallest diameter between the ribs or protrusions of the package. In the original configuration, the outermost diameter of the flared end is in the end of the catheter farthest away from the tip, that is the distal end of the catheter. Thereby, when the flared end is subjected to a pushing force in the direction opposite the removal direction of the catheter from the package, the flared end will be caught against a rib or protrusion in the package. If the pushing force exceeds a predetermined level, the flared end will be adapted to fold around itself so it faces in the opposite direction. In this position, the catheter will be able to be pushed back into the package almost without resistance. However a certain pulling force will be needed to unfold the flared end to the original configuration.

DETAILED DESCRIPTION OF THE INVENTION

In a first aspect, the invention relates to a urinary catheter kit comprising a package for a catheter having a storage space adapted for storing the catheter a urinary catheter having a proximal end with a tip and a distal flared end, where the tip is adapted for being inserted through the urethra and all the way into the bladder of the user, and the flared end is adapted for being connected to a tube for leading urine away from the catheter, the storage space being generally tubular and being provided with interior protrusions defining a smallest diameter of the storage space at the protrusions, the flared end having a largest diameter of the catheter larger than the diameter of an insertable part of the catheter, wherein the largest diameter of the catheter is larger than the smallest diameter of the storage space.

A urinary catheter kit as mentioned above, will be able to prevent the catheter from being pushed back into the storage space of the package. Thereby, the catheter kit will clearly indicate whether it has been used or not. Furthermore, the package will be able to function as backstop when the catheter is inserted into the urethra.

The package can be made in a number of configurations. In one embodiment, the package is made of a material that is gas impermeable. If a liquid swelling medium is provided inside the package, it may be advantageous that the package is made of a gas impermeable material, such that any diffusion of the liquid swelling medium is reduced or prevented and the catheter may be maintained in a wetted condition for a significant time period. A significant time period may for example be the shelf-life of the urinary catheter kit, which may be a period of approximately 6 months to approximately 5 years. An example of a material suitable for use is Polyethylene (PE).

In one embodiment, the storage space is shaped as a spiral. In other words, the storage space of the package is helical and may be shaped as an Archimedes spiral. This type of package makes a very compact catheter kit that is easy to carry along and keep in a handbag, a pocket or the like.

In another embodiment the package is elongated. In a related embodiment, the package is a corrugated element with side walls comprising alternating ridges and grooves.

The alternating ridges and grooves may increase the flexibility of the side wall of the corrugated tubular element, compared with a tubular element not having alternating ridges and grooves. In order to provide the package with a wall of flexible material, it may be provided as a side wall having alternating ridges and grooves in a radial direction of the central longitudinal axis of the package. This means that the thickness of the material may be increased in order to provide a more gas impermeable side wall, without having to compromise significantly on the flexibility of the package.

The flexibility of the package may be approximately 200 MPa. Thereby the package will be flexible but without being too bendable. The thickness of the package will for Polyethylene typically be between approximately 0.5 mm and approximately 0.8 mm.

The catheter may be a regular intermittent urinary catheter with an insertable length of approximately 80 mm to approximately 150 mm. Typically, the catheter will be provided with drainage eyelets at the tip end. Furthermore, the catheter will have an interior lumen to transport the urine from the tip to the connector end.

The catheter may be coated with a hydrophilic coating for provision of a low friction surface. A low friction surface reduces the risk of maceration of the internal walls of the urethra.

In an embodiment, the catheter may be packed for storage and/or transport with a liquid swelling medium for wetting the hydrophilic coating and for maintaining the hydrophilic coating in a fully hydrated state during storage and/or transport. By arranging a liquid swelling medium maintaining the hydrophilic coating in a fully hydrated state during storage and/or transport the user may be provided with a ready to use catheter that may be used directly after removing the telescopic device from its package. Furthermore, the user is not required to bring any accessories, such as lubricating gel or an external source of liquid swelling medium for the preparation of the catheter.

The rigidity of the catheter and the angle at the flared end may be selected so that the two properties in combination allow the flared end of the catheter to be bent in the direction towards the tip. This means that the flared end will be able to flip over. The ability to do that is controlled by both the rigidity of the material and the steepness of the taper at the flared end. If the angle is very low compared to the longitudinal direction of the catheter, the rigidity will need to be very low to enable the end to flip over. If the angle is high (close to 90 degrees), the rigidity can be much higher and still then end will be able to flip over.

Thus, the flared end of the catheter will be able to bend when subjected to a pushing force exceeding a predetermined level. This level will typically be around 4-10 N preferably 5 N for regular urinary catheters. The pushing force may be lower for thin catheters to be used for children and larger for the thickest types of catheters. This pushing force corresponds to the force usually required for inserting catheters into urethras. When the level of force required getting the flared end to flip over is selected to correspond to the usual insertion force, the flared end and the protrusions of the package will function as a safety measure during insertion. If the pushing force at the catheter gets too high, the flared end will flip over and send a signal to the user that there may be a constriction or other problem during insertion. Thus the user will be prevented from pushing too hard and thereby damaging the internal mucosa of the urethra.

The rigidity (measured as flexural modulus) will typically be between approximately 50 MPa and approximately 200 MPa.

The angle of the flared end with respect to the longitudinal direction may be approximately 45 degrees. Values around 45 degrees are suitable for a rather flexible catheter, that is a catheter having a flexural modulus in the lower end such as between 50 and 100 MPa. For a more rigid catheter, the angle should be steeper so it can be bent to face in the opposite direction. For such a catheter, values of approximately 75 degrees should be selected. The adaptation of the angle and the rigidity of the catheter are within the skills of a skilled person. Selecting an angle different from (lower than) 90 degrees has the effect that the force required to remove the catheter from the package will be less than the force required to get the flared end to flip over so that the catheter can be re-entered into the package.

The catheter may be made of a material such as Silicone or PolyUrethane.

The flared end of the catheter may be integral with the catheter. Alternatively, the flared end may be made as a separate element and attached to the catheter.

A flared end integral with the catheter is easy and fast to manufacture, because the catheter and flared end can be manufactured in fewer steps. The catheter will be extruded from the tip. Following that the end will be heated and during the heating process the end will be flared. This is one way of forming the catheter, however other ways are also possible.

The internal ribs of the package are made of the same material as the package. The material must be relatively, it should at least be more rigid than the flared end to be able to provide a force to the flared end.

The number of ribs can be anything between 4 and 20. For most users, approximately 10 ribs will be enough to provide the insertion aid. The ribs are at least approximately 0.2 mm in the direction extending out from the wall of the package. This corresponds to the thickness of the catheter and is thus enough to provide a backstop function.

When the package is helically shaped, the ribs need only be present in the outermost wall of each winding. This is because the catheter will seek to unfold itself to a straight configuration, thereby causing the flared end to be in contact with the outermost wall of each winding while the catheter is removed from the package.

The package may function as an insertion guide for the catheter. This is possible because the ribs of the package function as a stopper for the catheter and prevent it from being pushed back into the package.

Due to close-fitting the urine exiting the catheter is prevented from exiting the package in the front end of the package.

The package may be provided with means for preventing the catheter to be completely removed from the package. Thus the catheter kit has a position in which the catheter is fully extended. The means for preventing complete removal may be in form of larger ribs extending transversely into the package from the wall. For a spiral shaped package, a cavity may be provided into which the flared end fits. This cavity may have an extension to an outlet from the package.

When a catheter kit, as previously described, is used, the urine may start flowing before the catheter is fully extended to the proximal end of the package. For an elongated package, this is not a problem because the urine flows along the length of the package and exits at the distal end. However, for a spiral-shaped package, this may be a problem if urine flow commences before the flared end is fitted in the cavity. Only in this position, will the urine flow to the outlet from the package. If the flared end is within the spiral shape the urine will end up in the centre of the spiral. To overcome this, the package may be provided with a by-pass for letting urine pass from the centre to the outlet from the package. This by-pass may be in form of a channel extending across the spiral. However, other solutions are also possible, such as a tube.

DETAILED DESCRIPTION OF THE DRAWING

The invention is now explained more in detail with reference to the drawings showing preferred embodiments of the invention. However, it should be understood that the detailed description and specific examples, while indicating at least one preferred embodiment of the invention, are given by way of illustration only, since various changes and modifications within the spirit and scope of the invention will become apparent to those skilled in the art from this detailed description.

Figure 1:
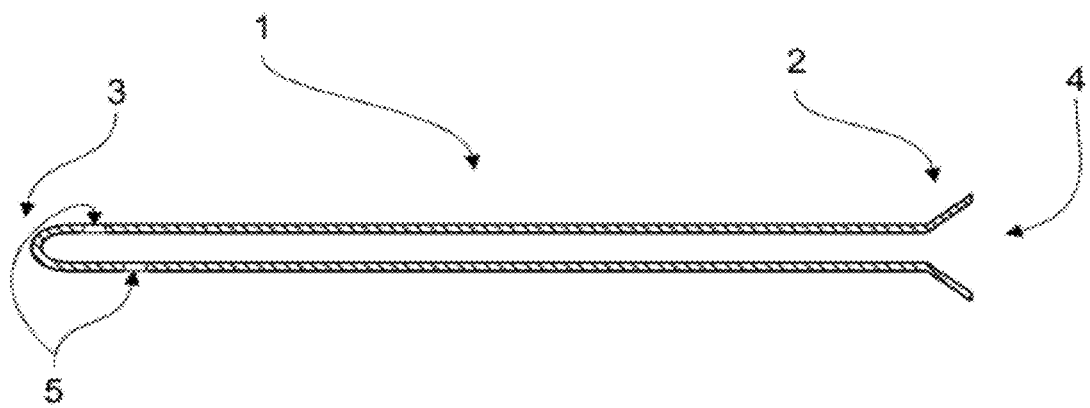
FIGS. 1 and 2 illustrate a catheter with a flared end.
Figure 2:
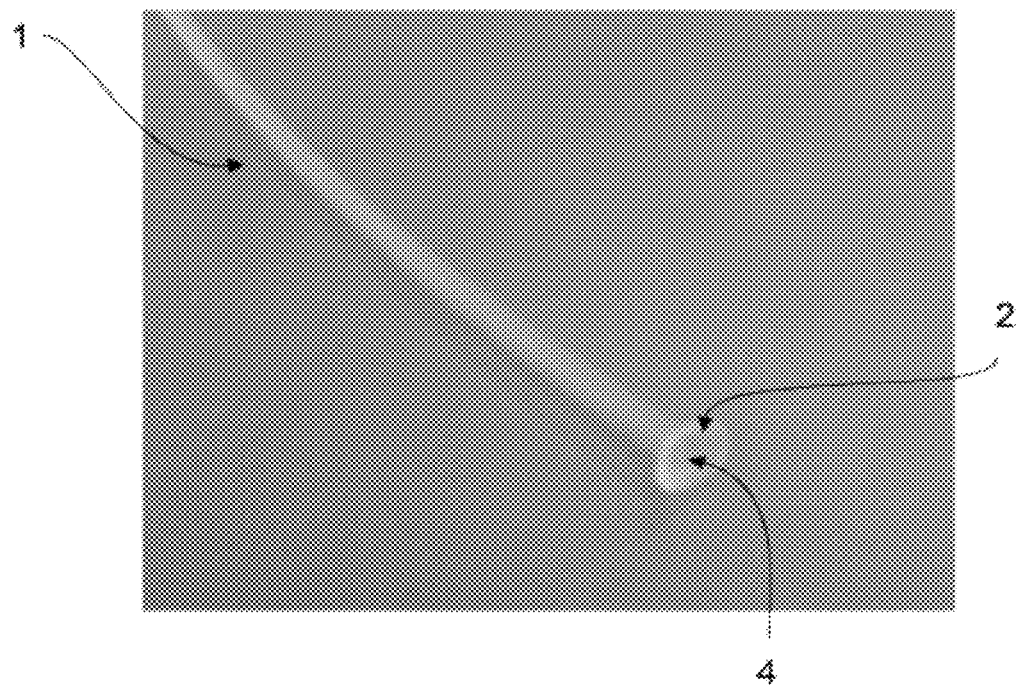

FIGS. 1 and 2 illustrate a catheter 1 with a flared end 2 that forms part of a kit (not shown in this figure) according to the invention. In FIG. 1, the catheter 1 is illustrated in cross-section, and in FIG. 2 a photograph of the distal end of the catheter is shown. The catheter comprises a tubular element with a proximal end 3 and a distal end 4. In the proximal end 3 (the insertion end), there are eyelets 5. In FIG. 1, two eyelets 5 are shown—however, there may be only one eyelet or more than two eyelets. The flared end 2 is provided in the distal end 4. The drawing in FIG. 1 is not to scale; a urinary catheter (particularly for males) will typically be longer compared to the width. FIG. 1 also illustrates the angle theta θ between the flared end and the remainder of the catheter.

Figure 3:
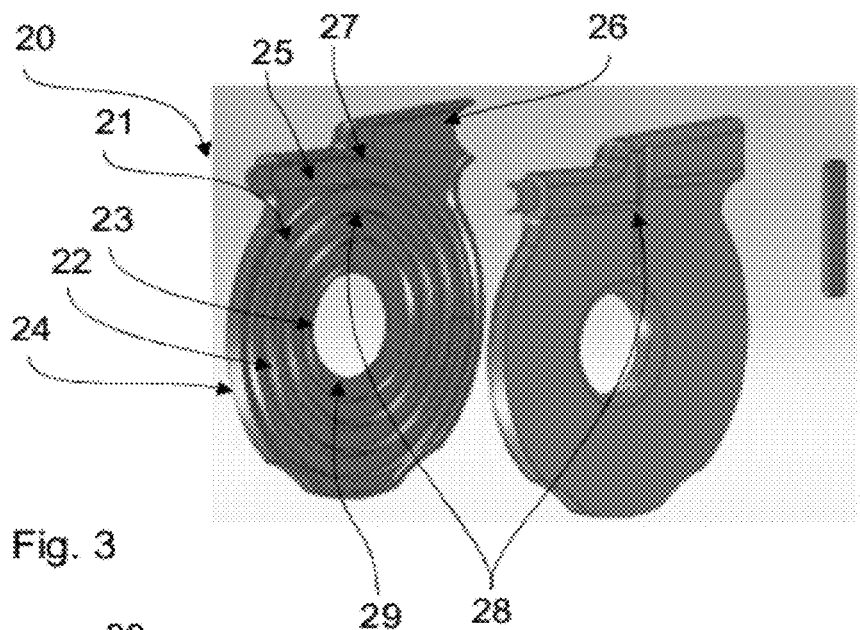
FIG. 3 illustrates one embodiment of a package.

FIG. 3 illustrates a package 20 that may be used in a kit according to the invention. This package 20 is a package with a spiral-shaped storage space 21 for a catheter defined by spiral-shaped walls 22. The spiral-shaped storage space 21 commences at an inner periphery 23 near the centre of the package and terminates at the outer periphery 24. At the termination, the package 21 is provided with a cavity 25 adapted for receiving the connector of a catheter, when the catheter is fully extended. In this position, the connector from a catheter will communicate with an outlet 26 from the package through a channel 27 connecting the outlet 26 and the cavity 25. The channel 27 may just be a hole in the wall 22 defining the storage space 21. The outlet 26 may be shaped as a tapered outlet so that it defines a receiving space for a connection to a tube.

The package 20 may further be provided with a by-pass 28 connecting the central storage space 29 at the centre 23 of the package with the outlet 26. As described earlier, such a by-pass allows urine, which has entered into the storage space 21, to exit the storage space 21 through the by-pass 28 and the outlet 26. The by-pass may be in the form of holes in the spiral-shaped walls 22.

Figure 4:
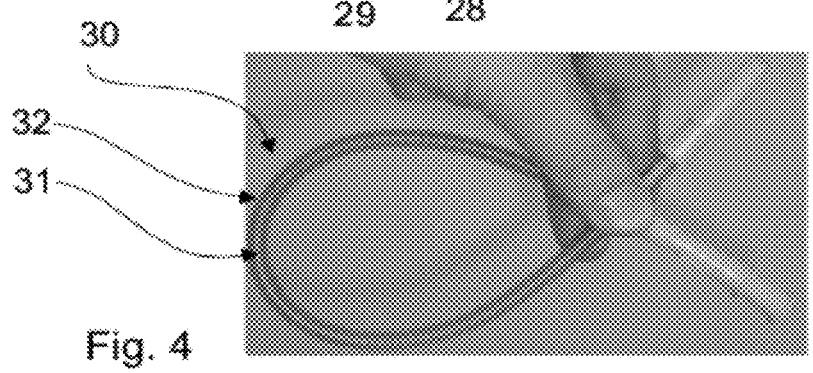
FIG. 4 illustrates another embodiment of a package.

FIG. 4 illustrates another type of package 30 that may form part of a kit according to the invention. This type of package 30 comprises a storage space 31 inside a tubular corrugated element 32. A corrugated package 30 allows the package including the catheter to be folded or rolled into a more compact figuration, as shown in the figure.

Figure 5A:
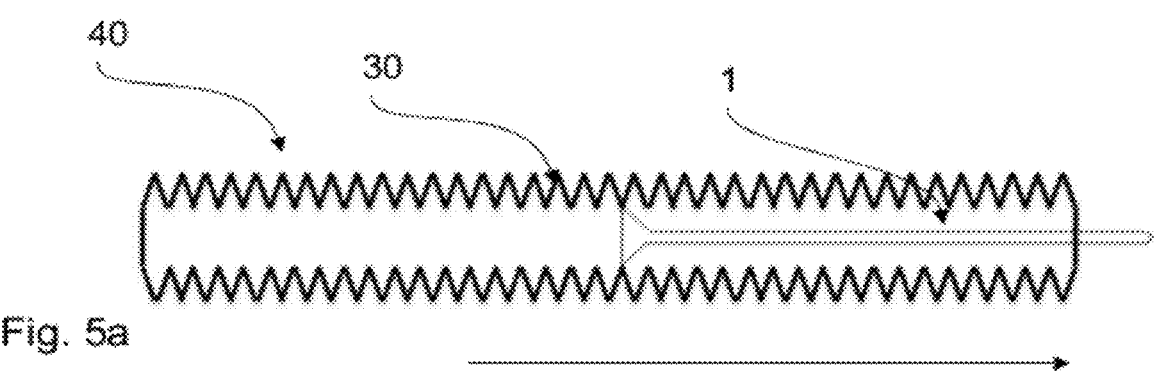
FIGS. 5a and 5b illustrate a kit comprising a catheter and a package.
Figure 5B:
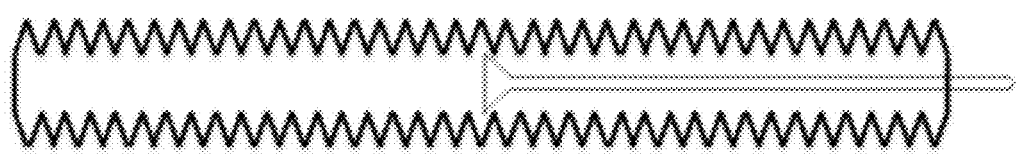

FIGS. 5A and 5B illustrates a kit 40 according to the invention. The kit 40 includes a corrugated package 30 as in FIG. 4 in combination with a catheter 1 as in FIG. 1. The catheter has a flared end 2 with an outer diameter slightly larger than the smallest inner diameter of the package 30 as shown in FIG. 5B. In FIG. 5A the flared end 2 of the catheter is compressed slightly as it passes one of the corrugations in the package 30. If the catheter is pulled out of the package, that is, in the direction of the arrow in the drawing, then the flared end 2 will be compressed slightly as it passes each corrugation. When the user tries to push the catheter into the package, in the direction against the arrow, then the flared end 2 will be caught against one of the corrugations and initially resist the pushing. If the pushing force exceeds a certain level (5-10 N) the flared end 2 will turn so it faces in the direction of the tip of the catheter, and the user will be able to push the catheter into the package.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:
1. A kit of parts comprising:
a urinary catheter having a tubular section sized to a first diameter and attached between a proximal end insertable into a bladder and a flared distal end having a diameter that is wider than the first diameter;
a package including a storage space provided to retain the urinary catheter, the storage space is defined by a wall organized in a spiral pattern with a space provided between the wall and an adjacent portion of the wall organized in the spiral pattern, the space is sized to receive the first diameter of the tubular section and the flared distal end of the urinary catheter in sliding engagement, and the spiral pattern terminates at an outer periphery of the package;
a cavity formed in an outer periphery of the package, and the spiral pattern terminates at the cavity formed in the outer periphery of the package; and
an outlet provided separately from the cavity, with a channel connecting the outlet and the cavity, and the outlet provided to allow urine to exit the package;
wherein the spiral pattern is configured to ensure contact between the flared distal end and the wall that is organized in the spiral pattern to thus prevent the urinary catheter from being pushed back into the storage space during insertion of the urinary catheter into the bladder;
wherein the cavity is sized to prevent the flared distal end of the urinary catheter from exiting the package.
2. The kit of parts according to claim 1, wherein the package is made of a material that is gas impermeable.
3. The kit of parts according to claim 1, wherein the urinary catheter is coated with a hydrophilic coating providing a low friction surface.

4. The kit of parts according to claim 3, wherein the urinary catheter is further provided with a liquid for wetting the hydrophilic coating and for maintaining the hydrophilic coating in a fully hydrated state during storage transport.

5. The kit of parts according to claim 1, wherein the flared distal end of the urinary catheter is integral with the urinary catheter.

6. The kit of parts according to claim 1, wherein the flared distal end is a separate element attached to the urinary catheter.

7. The kit of parts according to claim 1, wherein the outlet is tapered to define a receiving space for a connector that is adapted for connection to the flared distal end of the urinary catheter.

8. The kit of parts according to claim 1, wherein the wall is provided with ribs that extend outward from the wall.

9. The kit of parts according to claim 8, wherein the number of ribs is between 4 and 20.

10. The kit of parts according to claim 1, wherein the package includes a urine by-pass formed in the wall and communicating with the outlet.

11. The kit of parts according to claim 10, wherein the urine by-pass includes a plurality of holes formed in the wall.

\* \* \* \* \*